(12) United States Patent
Buan et al.

(10) Patent No.: US 12,161,794 B2
(45) Date of Patent: Dec. 10, 2024

(54) NEGATIVE PRESSURE DEVICE HAVING OXYGEN SCAVENGER AND VOLUME REDUCTION

(71) Applicant: Aatru Medical, LLC, Cleveland, OH (US)

(72) Inventors: John Buan, Maple Grove, MN (US); Richard L. Middaugh, Rocky River, OH (US); Timothy Wojciechowski, Westlake, OH (US); Thomas E. Lash, Chardon, OH (US)

(73) Assignee: Aatru Medical, LLC, Cleveland, OH (US)

( * ) Notice: Subject to any disclaimer, the term of this patent is extended or adjusted under 35 U.S.C. 154(b) by 593 days.

(21) Appl. No.: 17/265,617

(22) PCT Filed: Aug. 27, 2019

(86) PCT No.: PCT/US2019/048303
§ 371 (c)(1),
(2) Date: Feb. 3, 2021

(87) PCT Pub. No.: WO2020/046907
PCT Pub. Date: Mar. 5, 2020

(65) Prior Publication Data
US 2021/0299347 A1  Sep. 30, 2021

Related U.S. Application Data

(60) Provisional application No. 62/723,772, filed on Aug. 28, 2018.

(51) Int. Cl.
*A61M 1/00* (2006.01)
*A61B 46/00* (2016.01)
(Continued)

(52) U.S. Cl.
CPC .......... *A61M 1/962* (2021.05); *A61B 46/40* (2016.02); *A61F 13/0206* (2013.01); *A61F 13/05* (2024.01); *A61M 2202/0208* (2013.01)

(58) Field of Classification Search
CPC ... A61F 13/00068; A61F 13/05; A61M 1/962; A61M 1/80
See application file for complete search history.

(56) References Cited

U.S. PATENT DOCUMENTS

| 4,523,579 A | 6/1985 | Barry |
| 8,353,928 B2 | 1/2013 | Joshi |

(Continued)

FOREIGN PATENT DOCUMENTS

| WO | 2017075381 | 5/2017 | |
| WO | WO-2017075381 A1 * | 5/2017 | ............ A61F 13/00 |
| WO | 2020046935 | 3/2020 | |

OTHER PUBLICATIONS

Supplementary EP Search Report filed in EP 19 85 3606 dated May 13, 2022.
(Continued)

*Primary Examiner* — Susan S Su
*Assistant Examiner* — Meagan Ngo
(74) *Attorney, Agent, or Firm* — RANKIN, HILL & CLARK LLP

(57) ABSTRACT

A negative pressure tissue treatment system useful for negative pressure therapy includes a drape, a gasket material, a reactor housing, a reactor, and any fluid connection(s). The drape covers the skin of a patient and maintains negative pressure under the drape. The gasket material cooperates with the drape to define an enclosed volume that is scaled by the gasket material. The reactor housing defines a closed chamber in fluid communication with the enclosed volume, and the reactor is disposed in the reactor housing. The reactor consumes oxygen from a system volume defined by (Continued)

the enclosed volume, closed chamber, and/or any fluid connection(s). As a result of the oxygen consumption, the system volume is reduced to between about 95% to about 80% of the initial system volume.

14 Claims, 3 Drawing Sheets

(51) Int. Cl.
*A61F 13/0206* (2024.01)
*A61F 13/05* (2024.01)

(56) References Cited

U.S. PATENT DOCUMENTS

| | | | |
|---|---|---|---|
| 8,945,030 B2 | 2/2015 | Weston | |
| 10,046,095 B1 | 8/2018 | Middaugh | |
| 2005/0070835 A1* | 3/2005 | Joshi | A61M 1/962 |
| | | | 602/41 |
| 2007/0066946 A1* | 3/2007 | Haggstrom | A61M 1/966 |
| | | | 604/313 |
| 2009/0299341 A1* | 12/2009 | Kazala, Jr. | A61F 13/0223 |
| | | | 604/543 |
| 2014/0109890 A1 | 4/2014 | Pedicini | |
| 2015/0073361 A1* | 3/2015 | Pratt | A61M 1/882 |
| | | | 156/60 |

OTHER PUBLICATIONS

International Search Report filed in PCT/US2019/048303 mailed Nov. 15, 2019.

* cited by examiner

NEGATIVE PRESSURE DEVICE HAVING OXYGEN SCAVENGER AND VOLUME REDUCTION

BACKGROUND

Negative pressure wound therapy (NPWT) is well established for treatment of chronic and hard-to-heal wounds, and to reduce the incidence of post-surgical incision scarring and infections. Commercially available systems employ an external electromechanical pump, power supply, and controller attached to the wound dressing by a hose. Negative pressures of 120 mmHg and 80 mmHg (internal pressures of 640 mmHg and 680 mmHg, respectively) are commonly accepted as preferred ranges for many situations. Use of an electromechanical pump requiring a power supply and controller adds significant cost and degrades patient lifestyle because of apparatus bulk, weight, and noise.

Use of an oxygen chemical scavenger to produce negative pressure relative to atmosphere in a fixed volume system is considerably less expensive, requires no power supply, and is silent in operation. However, an oxygen chemical scavenger naturally produces a negative pressure of 150-160 mmHg, or internal pressure of 590-600 mmHg (depending on relative humidity, RH) by removal of the oxygen that constitutes 21% of dry air.

SUMMARY

According to one aspect, a negative pressure tissue treatment system comprises a drape that is a flexible material capable of maintaining a negative pressure underneath the drape upon application of a vacuum. A gasket material is secured on a skin-facing surface of the drape. The gasket material together with the drape define an enclosed volume beneath the drape and surrounded by the gasket material when the drape is affixed to skin around a tissue site. A reactor is in fluid communication with the enclosed volume. The enclosed volume defines a system volume. The reactor is configured to consume oxygen from the system volume. The drape is configured such that the system volume reduces from an initial system volume toward a reduced system volume that is between about 95% and about 80% of the initial system volume as a result of the reactor consuming oxygen from the system volume.

According to another aspect, a negative pressure tissue treatment system comprises a drape formed of a flexible material capable of maintaining a negative pressure underneath the drape upon application of a vacuum. A gasket material is secured on a skin-facing surface of the drape. The gasket material together with the drape define an enclosed volume beneath the drape and surrounded by the gasket material when the drape is affixed to skin around a tissue site. A reactor housing defines a closed chamber in fluid communication with the enclosed volume. A reactor is positioned in the closed chamber and is configured to consume oxygen. The closed chamber and the enclosed volume define a system volume. The drape and the reactor housing are configured such that the system volume reduces from an initial system volume toward a reduced system volume that is between about 95% and about 80% of the initial system volume as a result of the reactor consuming oxygen from the system volume.

DETAILED DESCRIPTION

The invention is not limited in its application to the details of construction and arrangement of components provided in the following description or illustrated in the attached drawings. The invention is capable of other embodiments and being practiced in various manners. The phraseology and terminology used herein is for the purpose of description and should not be regarded as limiting. Moreover, the use of "including," "comprising," or "having" and variations thereof is meant to encompass the items listed thereafter and equivalents thereof as well as additional items. The present disclosure generally relates to negative pressure-type wound systems, but the system described herein need not always be used with wound therapy and can be used in other applications.

For 50% RH at room temperature, water vapor pressure is about 9 mmHg. For dry air, removal of 21% oxygen will produce a negative pressure of 158 mmHg (760 mmHg-9 mmHg=751 mmHg). While this is still regarded as within the therapeutic range, lower negative pressures relative to atmosphere are often preferred as more comfortable for the patient and less likely to cause tissue stress when applied and removed.

It is recognized that a dressing sealed to patient skin will likely contain a higher water vapor pressure than those discussed below, since local atmospheric RH will vary, the skin will have a near-constant water vapor pressure and the temperature within the system will be somewhat closer to body temperature. These variables will have only a minor effect on the quantitative calculations below.

Allowing the NPWT system volume to decrease controllably under negative pressure can produce a controlled negative pressure less than the "natural" 150-160 mmHg (internal pressure 605±5 mmHg). As shown in the calculations below, a volume reduction of 5%-6% will produce a negative pressure of about 120 mmHg, and a volume reduction of about 11% will produce a negative pressure of about 80 mmHg.

$P_1V_1=P_2V_2$ where P1=605 mmHg (155 mmHg negative pressure)

If $V_2=0.945V_1$ (5.5% volume reduction), then $P_2=P_1(V_1/V_2)=605 (V_1/0.945V_1)$.

$P_2=605/0.945=640$ mmHg and 760−640=120 mmHg negative pressure.

If $V_2=0.89V_1$ (11% volume reduction), then $P_2=605/0.89$. $P_2=680$ mmHg and 760−680=80 mmHg negative pressure.

Figure 1:
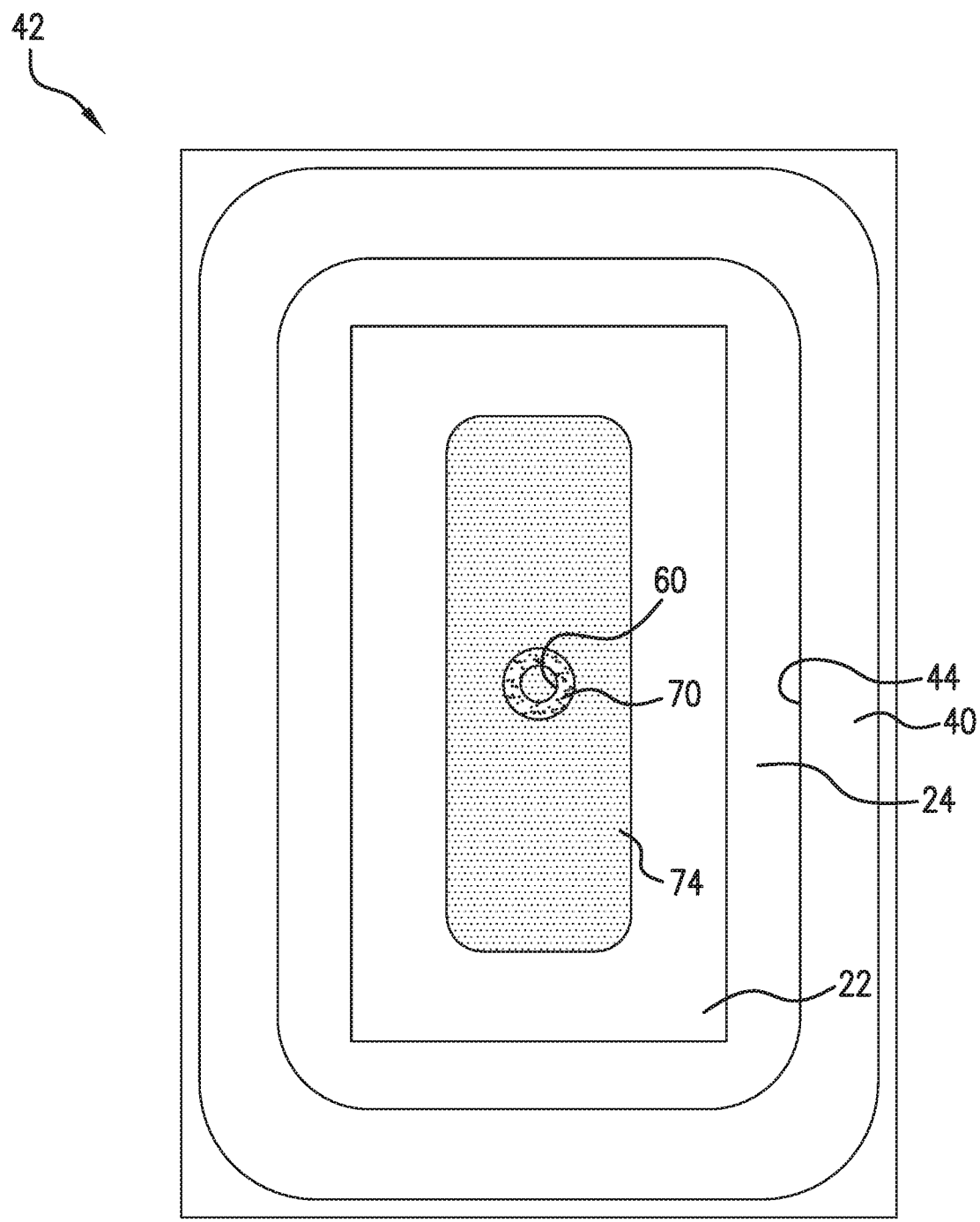
FIG. 1 is a schematic plan view of an example of a dressing for a negative pressure system according to the present disclosure.
Figure 2:
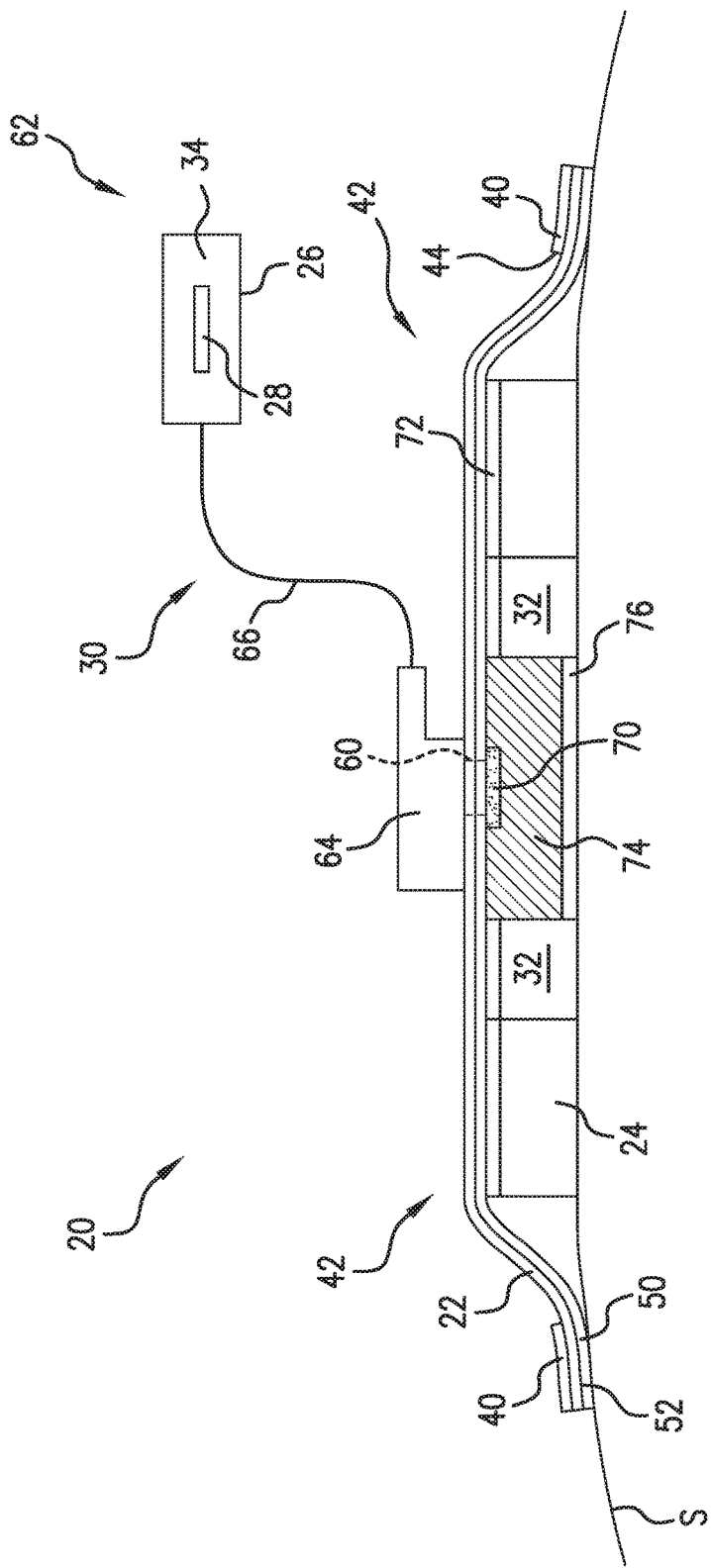
FIG. 2 is a schematic cross-sectional view of the negative pressure system prior to oxygen being removed from the system.
Figure 3:
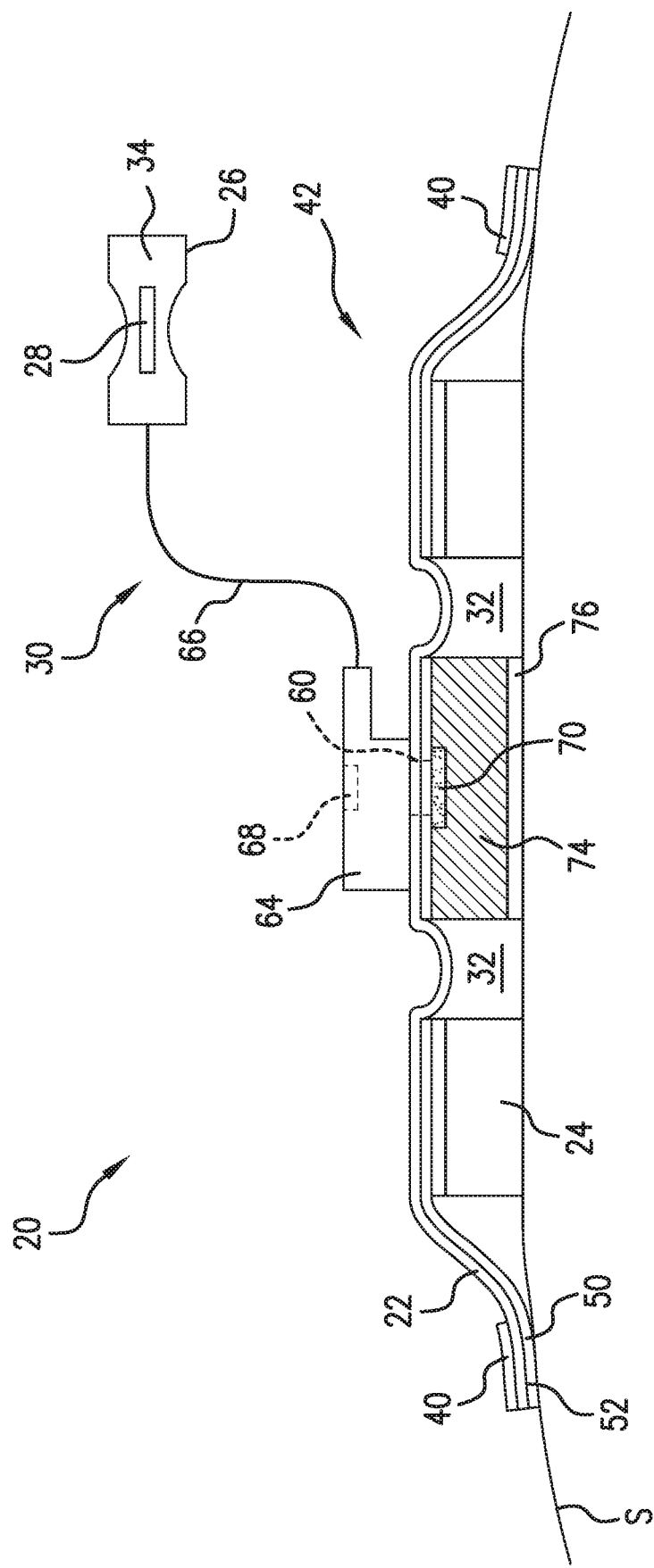
FIG. 3 is a schematic cross-sectional view of the negative pressure system after oxygen has been removed from the system.

With reference to FIGS. 1 and 2, a negative pressure tissue treatment system 20 includes a drape 22, a gasket material 24, a reactor housing 26, a reactor 28, and fluid connections 30 (depicted schematically). The negative pressure tissue treatment system 20 can include further components that will be described in more detail below. The drape 22 is made of a flexible material capable of maintaining a negative pressure underneath the drape 22 upon application of a vacuum. The gasket material 24 is positioned underneath the drape 22 when the drape 22 is affixed to skin S and defines an enclosed volume 32 beneath the drape 22 and surrounded by the gasket material 24 when the drape 22 is affixed to skin S around a wound, surgical incision, or other tissue site (hereinafter simply referred to as a "tissue site") so as to maintain a negative pressure environment beneath the drape 22 and around the tissue site for extended periods of time, and also allows easier handling for placement of the dressing onto the skin. The reactor housing 26 defines a closed chamber 34 in fluid communication with the enclosed volume 32 via the fluid connections 30. The reactor 28 is positioned in the closed chamber 34 and is configured to consume oxygen. The closed chamber 34, the enclosed volume 32 and the fluid connections 30 define a system volume, i.e., a volume of air from which the reactor 28 consumes oxygen. The drape 22, the reactor housing 26 and/or the fluid connections 30 is/are configured such that the system volume reduces from an initial system volume toward a reduced system volume that is between about 95% and about 80% of the initial system volume as a result of the reactor 28 consuming oxygen from the system volume.

The drape 22 can be a thin film capable of maintaining a negative pressure underneath the drape 22 upon application of a vacuum. The thin film from which the drape 22 is made can be substantially impermeable to liquids but somewhat permeable to water vapor, while still being capable of maintaining negative pressure underneath the drape 22. For example, the thin film material from which the drape 22 is made may be constructed of polyurethane or other semi-permeable material such as that sold under the Tegaderm® brand or 9834 TPU tape available from 3M. Similar films are also available from other manufacturers. Even though the film from which the drape 22 is made may have a water vapor transmission rate of about 836 g/m$^2$/day or more, these films are still capable of maintaining negative pressure underneath the drape 22 when an appropriate seal is made around the periphery of a tissue site. The drape 22 can be made from other flexible materials capable of maintaining a negative pressure underneath the drape 22 upon application of a vacuum, such as silicone, rubber and the like.

When the drape 22 is made from a thin film, the drape 22 can be cast onto a casting sheet 40, which can be made from paper, as part of a dressing 42. When the dressing 42 is assembled, the casting sheet 40 can be kiss cut to provide a casting sheet opening 44. The drape 22 can be made from a transparent material such the gasket material 24 can be visible within a "window" defined by the casting sheet opening 44 in the casting sheet 40.

A pressure-sensitive acrylic-based adhesive 50 can be applied on a skin-facing surface 52 of the drape 22. Other types of adhesives could be applied to the drape 22, however, a pressure-sensitive acrylic-based adhesive is known to provide strong initial tack that can last for a relatively long time, for example a few days, when in contact with the skin. The pressure-sensitive acrylic-based adhesive 50 can be applied over an entirety of the skin-facing surface 52 of the drape 22, which can also be useful to retain other components of the dressing 42 during assembly.

The drape 22 can also include an opening 60, which can allow for the connection of a vacuum source 62 to the dressing 42. The opening 60 can be cut through the casting sheet 40 (prior to removal of the portion of the casting sheet 40 which forms the casting sheet opening 44) and the drape 22 within an area surrounded by the gasket material 24. A fitting 64 (schematically depicted in FIG. 1) can be placed over the opening 60 and connect to a vacuum source 62, which includes the reactor 28, via a hose 66 (also schematically depicted in FIG. 1), which along with the fitting 64 can be a component of the fluid connection 30. An air-permeable/liquid-impermeable filter 70 can be provided covering the opening 60 in the drape 22. As shown in FIGS. 1 and 2, the air-permeable/liquid-impermeable filter 70 is positioned against the skin-facing surface of the drape 22; however, the air-permeable/liquid-impermeable filter 70 can be provided on an outer surface of the drape 22.

The gasket material 24 can be a silicone gel that is applied on a silicone gel backing film 72. When used for negative pressure wound therapy applications, it is desirable that the gasket material 24 have the following functional characteristics: (1) the material from which the gasket material 24 is made is extremely biocompatible, i.e., able to be worn for durations measured in days and weeks, with no discernible effects to the skin on which it resides, (2) the material should have mild adhesive properties, relative to skin, so that the material does not become unsealed as the wearer performs activities of daily living, and (3) the material should be flexible and conformable to adjust to the movements of the patient, while maintaining a "vacuum" seal at all times. Of the available biomedical materials, silicone gel is identified as a gasket candidate, such as the gel available from Polymer Science, Inc. as part number PS-1050. Other materials, such as hydrogel, could function as a sealing gasket but are not as biocompatible as silicone gel.

The vacuum source 62 includes the reactor 28, which is a chemical oxygen scavenger that removes oxygen from the air within the enclosed volume 32 so as to reduce the gas pressure within the enclosed volume by approximately 20%, unless there is a change in volume in the system volume. Since the vacuum source 62 in this embodiment includes the reactor 28, which is a chemical oxygen scavenger, any leakage around the enclosed volume 32 is important to prevent. The ingress of outside oxygen, which could use up the reactor 28 in the vacuum source 62, should be prevented from penetrating either through the drape 22 or the gasket material 24 or between the gasket material 24 and the skin S.

In FIG. 1, the reactor 28 is positioned in the closed chamber 34. The reactor 28 is in fluid communication via the fluid connection 30 and the opening 60 with the enclosed volume 32 beneath the drape 22 and surrounded by the gasket material 24 when the dressing 42 is affixed to skin S around the tissue site. The closed chamber 34, which is defined by the reactor housing 26, and/or the enclosed volume 32 typically does not communicate with ambient unless there is a leak in the negative pressure tissue treatment system 20. This is in contrast to known negative pressure systems which employ a mechanical pump that draws air from an enclosed volume through the mechanical pump into ambient. Leakage in these mechanical pump systems is not as critical since the mechanical pump typically can overcome the effect of a relatively small flow of air entering the enclosed volume by way of leakage in the system. In contrast, too much leakage when using the reactor 28 may result in the reactor 28 being consumed and no longer able to scavenge oxygen.

The drape 22, the reactor housing 26 and/or the fluid connection 30 is/are configured such that the system volume reduces from an initial system volume toward a reduced system volume that is between about 95% and about 80% of the initial system volume as a result of the reactor 28 consuming oxygen from the system volume. FIG. 2 depicts the drape 22 being drawn toward the skin S as a result of the reactor 28 consuming oxygen from the system volume, which reduces the volume of the enclosed volume 32. Since the drape 22 is not a rigid housing placed over the tissue site, the initial volume of the enclosed volume 32, i.e., prior to the reactor 28 consuming oxygen from the system volume, can reduce the system volume from the relatively larger initial system volume to the reduced system volume. In addition to or alternatively, the reactor housing 26 and/or the fluid connection 30 can reduce in volume as a result of the reactor 28 consuming oxygen from the system volume. FIG. 2 depicts the reactor housing 26 having side walls that draw in as a result of the reactor 28 consuming oxygen from the system volume and the fitting 64 including an elastic or resilient element (such as a dome-shaped element) 68 that draws in as a result of the reactor 28 consuming oxygen from the system volume. Each of these components, e.g., the drape 22, the reactor housing 26 and the fluid connection 30 can be configured such that the system volume reduces from an initial system volume toward a reduced system volume that is between about 95% and about 80% of the initial system volume as a result of the reactor 28 consuming oxygen from the system volume.

If desired, the dressing 42 can include an island of absorbent material 74 useful to absorb exudate from a wound. The island of absorbent material 74 can be applied onto the skin-facing surface 52 of the drape 22 and affix to the drape 22 via the pressure-sensitive acrylic-based adhesive 50. The island of absorbent material 74 has a smaller area than the drape 22 so as to leave a margin of adhesive-coated drape around the island of absorbent material 74. The absorbent material from which the island of absorbent material 74 is made can be a super absorbent polyester. Examples of such absorbent materials include a hydroactive wound pad available under the trademark Vilmed®. A silicone coating 76 can be provided on a skin-contacting side of the island of absorbent material 74, if desired, which is very compatible with skin and other tissue. As mentioned above, the drape 22 can be made from a transparent material such that the island of absorbent material 74 is visible when applying the dressing 42. As is evident in the embodiment depicted in FIG. 1, the casting sheet 40 is kiss cut around the area of the gasket material 24 so as to allow for the person placing the dressing 42 onto the tissue site to see both the gasket material 24 and the island of absorbent material 74 during placement of the dressing 42.

With reference back to FIG. 2, the island of absorbent material 74 can be spaced from the gasket material 24 at a predetermined distance, which can be a function of the system volume, so as to allow the drape 22 to be drawn toward the skin S between the island of absorbent material 74 and the gasket material 24 as oxygen is being removed from the system volume. The spacing between the island of absorbent material 74 and the gasket material 24 can be configured such that the system volume reduces from an initial system volume toward a reduced system volume that is between about 95% and about 80% of the initial system volume as a result of the reactor 28 consuming oxygen from the system volume based on the flexibility of the drape 22 and/or the compressibility of the absorbent material from which the island of absorbent material 74 is made.

Where the island of absorbent material 74 is compressible, its use to reduce the system volume and lower the negative pressure also mitigates some of the effect of absorbed exudate from a wound or incision. In a rigid system, e.g., one in which the drape is made from a rigid material, absorption of exudate will displace air volume, causing the net pressure to increase (and the negative pressure to decrease). If volume reduction is controlled by the net pressure on the system, lowering the air volume due to exudate will also increase the system volume due to the increased air pressure. Thus, the net loss of negative pressure will be less than that of a rigid volume system.

The reactor housing 26 can be configured such that its side walls, or another resilient or flexible component on the reactor housing 26, draws in as a result of the reactor 28 consuming oxygen from the system volume. The side walls or other resilient or flexible component on the reactor housing 26 can be configured such that the system volume reduces from an initial system volume toward a reduced system volume that is between about 95% and about 80% of the initial system volume as a result of the reactor 28 consuming oxygen from the system volume. The degree to which the side walls or other resilient or flexible component on the reactor housing 26 draws in or compresses so as to reduce the volume of the closed chamber 34 can be a function of the system volume so that the system volume reduces from the initial system volume toward a reduced system volume that is between about 95% and about 80% of the initial system volume as a result of the reactor 28 consuming oxygen from the system volume.

Similarly, the elastic or resilient element 68 on the fitting 64 can also be configured to draw in as a result of the reactor 28 consuming oxygen from the system volume. The degree to which the elastic or resilient element 68 draws in or collapses so as to reduce the volume of the fluid connection 30 can be a function of the system volume so that the system volume reduces from the initial system volume toward a reduced system volume that is between about 95% and about 80% of the initial system volume as a result of the reactor 28 consuming oxygen from the system volume.

Each of the drape 22, the reactor housing 26 and the fluid connection 30 can be configured such that the system volume reduces from an initial system volume toward a reduced system volume that is between about 95% and about 80% of the initial system volume as a result of the reactor 28 consuming oxygen from the system volume. In other words, the drape 22, the reactor housing 26 and the fluid connection 30 can all collapse to result in a reduction of system volume, or only one or two of the drape 22, the reactor housing 26 and the fluid connection 30 can collapse.

In addition, the drape 22 can be configured to collapse even further so that the reduced system volume approaches zero ml or cc. This can be beneficial in situations where negative pressure with respect to atmosphere need not be in the therapeutic range discussed above, but limiting the oxygen around the wound is desirable. For example, the reactor 28 can be placed in the enclosed volume 32 or in a chamber (similar to the closed chamber 34) having little or no volume. As the drape 22 collapses toward the skin S as a result of oxygen being removed from the enclosed volume 32, the enclosed volume 32 would reduce from an initial volume toward a reduced volume. As such, the pressure in the enclosed volume 32 would rise toward atmospheric pressure, but oxygen would be removed from the enclosed volume 32 and thus around the tissue site surrounded by the gasket material 24.

It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A negative pressure tissue treatment system comprising:

a drape formed of a flexible material capable of maintaining a negative pressure underneath the drape upon application of a vacuum;

a gasket material secured on a skin-facing surface of the drape, the gasket material together with the drape defining an enclosed volume beneath the drape and surrounded by the gasket material when the drape is affixed to skin around a tissue site;

a reactor in fluid communication with the enclosed volume; and a reactor housing defining a closed chamber for housing the reactor, the closed chamber is in fluid communication with the enclosed volume via a fluid connection, wherein the enclosed volume, the closed chamber and the fluid connection define a system volume, the reactor is configured to consume oxygen from the system volume, and the drape is configured such that the system volume reduces from an initial system volume toward a reduced system volume that is between about 95% and about 80% of the initial system volume as a result of the reactor consuming oxygen from the system volume.

2. The negative pressure tissue treatment system of claim 1, wherein the reactor housing includes a resilient component configured to be drawn into the closed chamber as a result of the reduction of the system volume.

3. The negative pressure tissue treatment of claim 2, wherein the resilient component is part of a side wall of the reactor housing.

4. The negative pressure tissue treatment of claim 2, wherein the resilient component is parts of opposed side walls of the reactor housing.

5. The negative pressure tissue treatment system of claim 1, wherein the fluid connection is configured to at least partially collapse as a result of the reduction of the system volume.

6. The negative pressure tissue treatment system of claim 5, wherein the drape includes an opening for connection of a fitting provided as part of the fluid connection, the fitting includes a resilient element configured to be drawn into the fitting as a result of the reduction of the system volume.

7. The negative pressure tissue treatment system of claim 1, wherein the drape is adapted to be drawn into the enclosed volume as a result of the reduction of the system volume.

8. The negative pressure tissue treatment system of claim 1, further including an island of absorbent material adhered on the skin-facing surface of the drape, the island of absorbent material spaced from the gasket material, and a spacing between the island of absorbent material and the gasket material defines at least a portion of the enclosed volume.

9. The negative pressure tissue treatment system of claim 8, wherein the drape is a thin film configured to be drawn toward the skin between the island of absorbent material and the gasket material as oxygen is being removed from the enclosed volume.

10. A negative pressure tissue treatment system comprising:

a drape formed of a flexible material capable of maintaining a negative pressure underneath the drape upon application of a vacuum;

a gasket material secured on a skin-facing surface of the drape, the gasket material together with the drape defining an enclosed volume beneath the drape and surrounded by the gasket material when the drape is affixed to skin around a tissue site;

a reactor housing defining a closed chamber in fluid communication with the enclosed volume;

a reactor positioned in the closed chamber and configured to consume oxygen, wherein the closed chamber and the enclosed volume define a system volume, wherein the drape and the reactor housing are configured such that the system volume reduces from an initial system volume toward a reduced system volume that is between about 95% and about 80% of the initial system volume as a result of the reactor consuming oxygen from the system volume, wherein the enclosed volume is in fluid communication with the closed chamber via a fluid connection, the fluid connection further defines the system volume.

11. The negative pressure tissue treatment system of claim 10, wherein the reactor housing includes a resilient component configured to be drawn into the closed chamber as a result of the reduction of the system volume.

12. The negative pressure tissue treatment of claim 11, wherein the resilient component is part of a side wall of the reactor housing.

13. The negative pressure tissue treatment system of claim 10, wherein the fluid connection includes a fitting secured in an opening provided in the drape, the fitting includes a resilient element configured to be drawn into the fitting as a result of the reduction of the system volume.

14. The negative pressure tissue treatment system of claim 13, wherein the resilient element is part of an exterior wall of the fitting.

* * * * *